United States Patent [19]

St. Vincent et al.

[11] Patent Number: 4,520,805

[45] Date of Patent: Jun. 4, 1985

[54] ABDUCTOR TURNTABLE

[75] Inventors: Valerie A. St. Vincent, 1750 Prefumo Cyn. Rd., #51, San Luis Obispo, Calif. 93401; Frank B. Heinen; Steven J. Rinell, both of San Luis Obispo, Calif.

[73] Assignee: Valerie St. Vincent, San Luis Obispo, Calif.

[21] Appl. No.: 460,592

[22] Filed: Jan. 24, 1983

[51] Int. Cl.³ .............................. A61F 3/00; A61F 5/00
[52] U.S. Cl. ................................ 128/80 R; 128/80 G; 269/328
[58] Field of Search ................. 128/75, 80 C, 84 C, 128/84 B, 88, 135, 89, 95, 87, 80 R, 80 A, 80 F, 80 G; 269/328

[56] References Cited

U.S. PATENT DOCUMENTS

| | | | |
|---|---|---|---|
| 2,052,990 | 9/1936 | Siebrandt | 128/88 |
| 3,643,938 | 2/1972 | Levasseur | 128/75 |
| 3,653,378 | 4/1972 | Reuther | 128/88 |
| 3,701,349 | 10/1972 | Larson | 128/89 R |
| 3,753,557 | 8/1973 | Kelley | 269/328 |
| 3,759,252 | 9/1973 | Berman | 269/328 |
| 4,276,875 | 7/1981 | Sandegard | 128/89 R |
| 4,323,060 | 4/1982 | Pecheux | 128/75 |

Primary Examiner—C. Fred Rosenbaum
Assistant Examiner—C. W. Shedd
Attorney, Agent, or Firm—Daniel C. McKown

[57] ABSTRACT

Apparatus that permits a hip surgery patient to be rotated to lie on his side while maintaining the affected leg in a desired degree of abduction and external rotation includes a splint portion that grasps the affected leg and that is secured to an elevating portion. The elevating portion includes a splint-mounting bar that is hinged to a stationary base that lies on the bed. The axis of the hinge is approximately colinear with the spine of the patient. The apparatus constrains the affected leg to move on an arcuate path as the patient is rolled onto his side whereby the affected leg swings to the elevated position. The elevating portion includes locking devices for maintaining the affected leg in the elevated position.

8 Claims, 16 Drawing Figures

ABDUCTOR TURNTABLE

BACKGROUND OF THE INVENTION

1. Field of the Invention

The present invention is in the field of medical equipment and more specifically relates to an apparatus for raising a patient's leg to an elevated position above the bed, for maintaining the leg in the elevated position, and for lowering the leg to the surface of the bed, all the while holding the leg in a chosen degree of abduction, fixed external rotation, and minimum flexion.

2. Some Definitions

Figure 12:
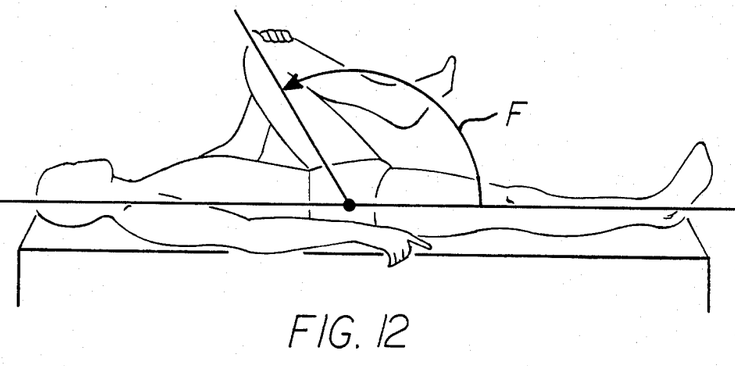
FIG. 12 is a diagram illustrating the concepts of flexion and extension.

As illustrated in the diagram of FIG. 12, FLEXION (F) is motion involving an increase of the angle between two bones at a joint. EXTENSION is the opposite of flexion and involves a decrease in the angle between the two bones.

Figure 13:
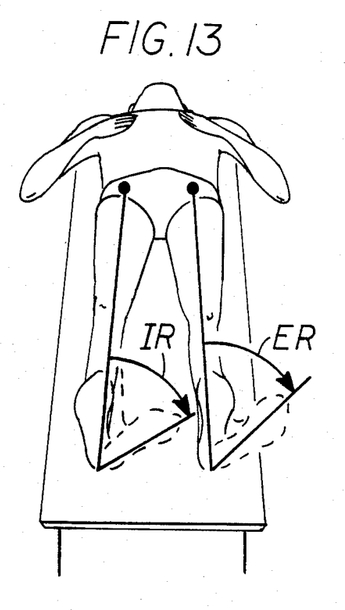
FIG. 13 is a diagram illustrating the concepts of internal and external rotation.

In INTERNAL ROTATION (IR) the toes of the foot are turned inward as shown in the diagram of FIG. 13. In EXTERNAL ROTATION (ER) the toes are turned outward.

Figure 14:
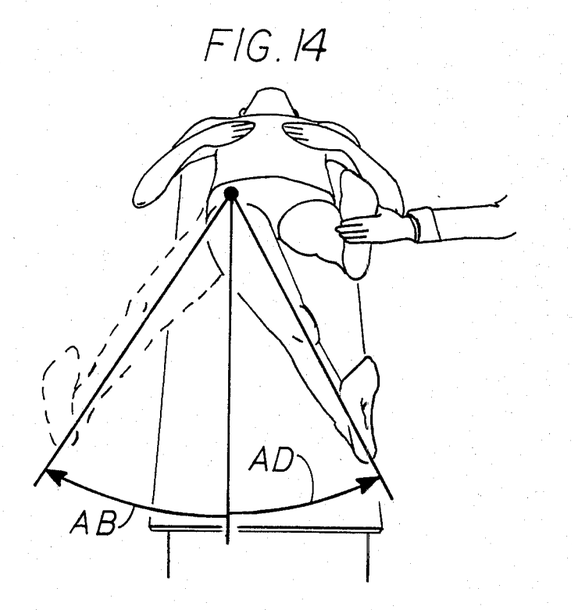
FIG. 14 is a diagram illustrating the concepts of abduction and adduction.

In ABDUCTION (AB) the leg is moved away from the midline of the body, as shown in the diagram of FIG. 14. The opposite of abduction is ADDUCTION (AD), in which the leg is moved toward the midline of the body.

ARTHROPLASTY is the artificial replacement of part or all of a joint surface.

3. The Prior Art

The human pelvis includes two ball-and-socket hip joints, right and left. The affected side is replaced to remedy severe conditions such as arthritis or because of bone fracture. Following such replacement surgery, the patient must avoid both adduction (the opposite of abduction) and internal rotation of the affected leg to prevent dislocation of the replaced hip joint. It is also essential that flexion of the affected hip and corresponding knee be minimized.

Figures 15, 16:
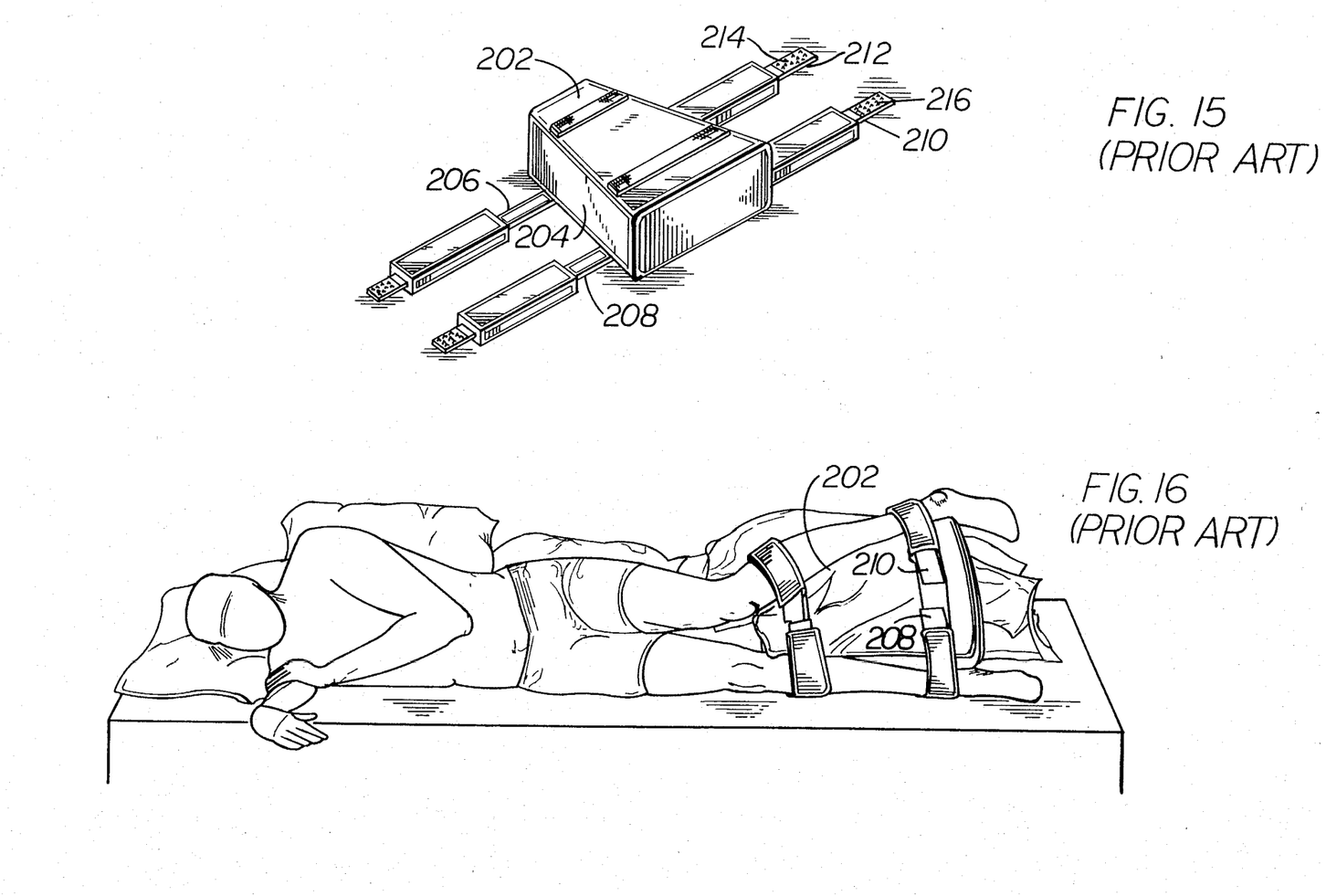

To prevent these dangerous movements from occurring, it has been conventional in the art to place a large thick triangular pillow 202 such as that shown in FIG. 15 between the patient's legs, as shown in FIG. 16, and to strap the legs against opposite sides 204 of the pillow by use of the straps 206, 208, 210, 212 which may be secured by VELCRO ® fasteners of which the pieces 214, 216 are typical.

Proper management of post operative patients requires patient movement, positioning and skin care. Without these, lung, circulatory, and skin problems may develop. Proper skin care includes eliminating pressure from high risk areas of the body. The most prominent of these areas are the heel, sacrum, buttocks, and greater trochanter (side of hips) regions. If pressure is not removed several times a day decubiti will surely result. Most Hip arthroplasties occur in people over the age of 60.

Thus proper management of the post-operative hip arthroplasty patient is highly complicated by the necessity of maintaining an abducted, externally rotated and minimally flexed position. Because the opposite of these movements are the most commonly assumed positions of people in bed, maintaining correct alignment of hip arthroplasties has been a difficult challenge since its beginning. The acute post-operative course lasts two to three weeks on the average.

Although the abductor pillow of FIGS. 15 and 16 was an easy and obvious method of caring for these patients, it has turned out to be far too simplistic and has actually created more problems than it has solved. Thus, it has now been abandoned by many hospitals and teaching facilities, and they have resorted to using standard pillows and literally hoping for the best.

The major inadequacies and dangers of the abductor pillow of FIGS. 15 and 16 are:

1. The pillow totally confines the uninvolved leg, which is unnecessary and complicates patient care.

2. Since the uninvolved leg is not painful, patients move it continuously and therefore pull the involved leg into flexed and adducted positions whenever the uninvolved leg moves into flexion or abduction.

3. The abductor pillow in no way restricts internal rotation or flexion of the involved hip. It also does not restrict in any way knee flexion which is crucial in preventing hip movement.

4. When rotation of the body toward the unaffected side is attempted there is no way of maintaining the body in this position other than propping pillows behind the entire length of the body. It must be remembered that with the pillow the affected foot sits about 18–24 inches off the bed. It is obvious how this position would be very difficult to maintain in an object which is motionless much less a person who is trying to move all the time.

5. While rotated to the side for 1 to 2 hours, 3 to 4 times a day, it has been impossible to prevent the patient from bending his knee. When this happens his hip flexes also, and since internal rotation has not been eliminated, dislocation of the affected hip frequently occurs. Constant patient surveillance by nursing staff would be the only way to prevent this occurrence and that is literally impossible.

6. While rotated, the uninvolved hip bears all the weight of the abductor pillow and the involved leg, and it also is immobilized if proper positioning is maintained. This patient discomfort is totally unnecessary.

7. In a supine or rotated position the straps on the pillow must be tight to prevent movement. This causes a high risk of peroneal nerve palsy which results in permanent foot drop, requiring a permanent short leg brace to correct. Peroneal nerve palsy results from excessive pressure to the nerve as it becomes very superficial at the outside aspect of the knee.

8. While rotated toward the uninvolved side the patient pulls the uninvolved leg forward in the effort to get comfortable. When this happens it pulls the involved leg downward to an adducted position, therefore without any degree of abduction and no prevention of internal rotation, dislocation frequently occurs during this attempted maneuver.

9. Use of the abductor pillow requires at least 2 nurses and frequently 3 or 4 to do the rotating maneuver, which is very difficult to organize in an acute hospital setting.

10. The abductor pillow requires the use of 4 to 6 pillows to maintain a rotated position. Storage of this many pillows is difficult in a patient's room. Also, and very importantly, these pillows become contaminated while not in use and usually are stacked in a chair because they fall and frequently get used by other patients in the meantime. Thus the risk of infection is greatly increased.

11. The abductor pillow invites decubiti, especially on both heels, sacrum and the buttocks. It actually promotes them on the heels because the weight of the pillow pulls the heels into the bed further.

Various workers in the art have proposed apparatus other than the conventional abductor pillow for treating hip dislocations. In U.S. Pat. No. 3,759,252, Berman shows an apparatus for treating hip dislocations in which the patient lies in a cradle shell with his knees held in an elevated position by a support bar which is adjustable in position to permit selection of the degree of flexion, which is maintained by the apparatus. The apparatus also includes a support yoke assembly for engaging about the top side of the patient's leg to secure the legs in a fixed degree of abduction. The apparatus of Berman includes no provision for rotating the patient onto his side.

In U.S. Pat. No. 3,815,589, Bosley describes a brace assembly for controlling the hip position of a child. The assembly includes a pair of thigh cuffs and a pair of calf cuffs, each cuff being generally semicircular in shape and suitably padded. The thighs of the child are positioned within the thigh cuffs and the calves are also fastened into their cuffs. The thigh and calf cuffs can be selectively rotated to desired orientations and locked in the desired orientations. The brace assembly allows for a variety of positions of the hip including abduction, external and internal rotation and some degree of flexion. There is little if any structural similarity between the apparatus of Bosley and that of the present invention.

In U.S. Pat. No. 3,730,177, Thum shows a device in which the motion of the patient's legs is yieldably opposed by tension belts or spring elements. The device does not hold the patient's calf and it is clear that the device produces flexion instead of avoiding it.

None of these workers in the prior art has addressed the problem of rotating the patient onto his side while maintaining a desired degree of abduction and external rotation and minimal flexion. As will be seen below, the apparatus of the present invention overcomes the difficulties associated with use of the conventional abductor pillow and provides a means for rotating the patient onto his side that is both safe and convenient.

SUMMARY OF THE INVENTION

The present invention includes apparatus for swinging the affected leg upward from the plane of the bed to an elevated position above the surface of the bed while maintaining the affected leg in a selected degree of abduction, fixed external rotation and minimal flexion. The apparatus includes a separable splint portion and an elevating portion. The splint portion consists of two elongated arched shells that constitute the sides of the splint and that are joined by a piano hinge aligned with the direction of elongation. In use, the splint is lined with a foam plastic sheet for comfort and the hinge is placed under the affected leg. Next, the shells that constitute the sides of the splint are closed about the leg and secured in the closed position by straps. In normal use, the splint portion extends from above the knee to below the knee.

When the affected leg of the patient is to be elevated, the elevating portion of the apparatus is placed on the surface of the bed and the splint is affixed to a movable part of the elevating portion. This movable part of the elevating portion is hinged to a base part of the elevating portion along an axis that is more or less colinear with the spine of the patient. The apparatus is adjusted so that the splint is held at the desired degree of abduction and external rotation even while the leg is not elevated. As the patient is rolled onto his side, the apparatus constrains the affected leg to rise along an arcuate path from the surface of the bed to an elevated position. In this manner, the desired degree of abduction and external rotation are maintained at all times as the patient is being rolled onto his side. Once the affected leg has reached the maximum desired degree of elevation, the elevating portion of the apparatus is locked to maintain the leg in that position. When the patient is to be returned to his back, the apparatus is unlocked and it constrains the affected leg to traverse the arcuate path in the opposite direction until the affected leg is again lying on the bed.

The apparatus includes an optional cage portion which can be affixed at the discretion of the physician to the elevating portion for the purpose of restraining the unaffected leg and using the unaffected leg to keep the apparatus from shifting on the bed.

In other embodiments, the apparatus is strapped to the mattress so that it cannot shift on the surface of the bed. In still other embodiments, portions of the apparatus are coated with a soft rubbery compound that prevents the apparatus from slipping on the surface of the bed.

Although this apparatus was designed to solve the problem of frequent dislocations (about 3%) following hip arthroplastic surgery, there is no reason why it could not be used on any person that is unable to or should not, for medical reasons, move a leg by himself.

Much of the design here was created to make patient care easier for the nursing staff. Pillows have been, for long history, a nurse's only tool for turning and positioning patients in bed. The apparatus of the present invention simplifies this procedure for nursing and it also maintains it where pillows, of any shape, never have.

The abductor turnable of the present invention adjusts to a neutral or normal body position, as well as the unusual but necessary body position needed after hip arthroplasty. The turntable, in a neutral position, allows for turning a patient in a normal comfortable position, while maintaining the secured leg in an immobilized state. This is frequently desired in such maladies as an open fracture, a burned leg, or even in a stroke victim. Thus, the apparatus of the present invention has many uses and is not limited to hip surgery patients.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 15 is a perspective view of an orthopedic wedge-shaped cushion of a type known in the prior art; and, FIG. 16 is a perspective view of the prior art cushion of FIG. 15 in use.

DETAILED DESCRIPTION OF THE PREFERRED EMBODIMENT

A major objective of the design of the abductor turntable was to achieve a very high degree of adaptability while at the same time keeping the structure reasonably simple and the technique for using the abductor turntable straightforward. The preferred embodiment shown in FIGS. 1-11 demonstrates that these objectives have been achieved.

The present invention is adaptable for use on patients of various heights and weights. It can be adjusted to fit legs of different circumferences.

The present invention permits a leg of the patient to be maintained at a chosen angle of abduction, at nearly a fixed angle of external or internal rotation, and in minimal flexion. Because the leg of the patient is maintained at the chosen attitude, undesirable conditions of adduction, rotation and excessive flexion are prevented from occurring.

Figure 1:
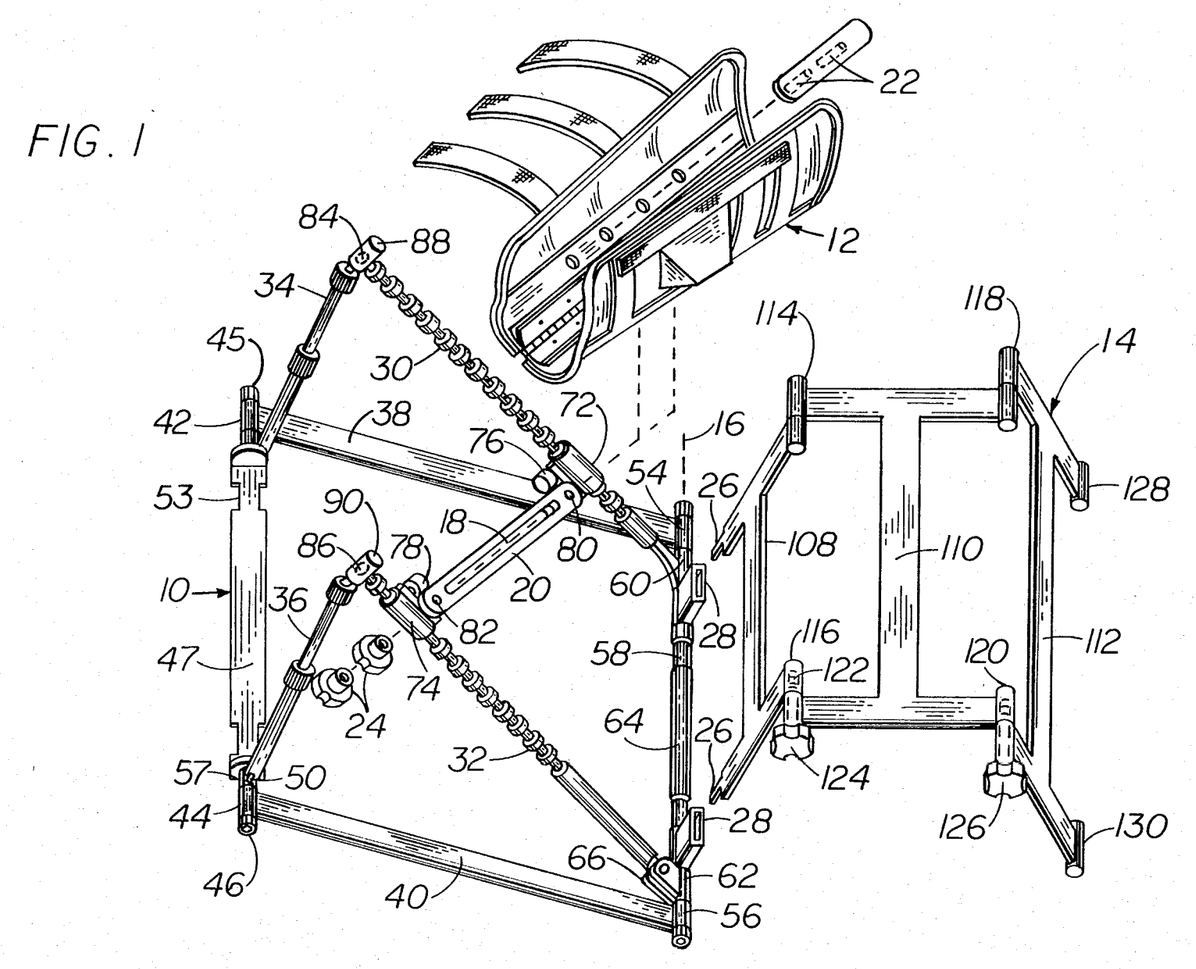
FIG. 1 is an exploded perspective view showing a preferred embodiment of the present invention.
Figure 2:
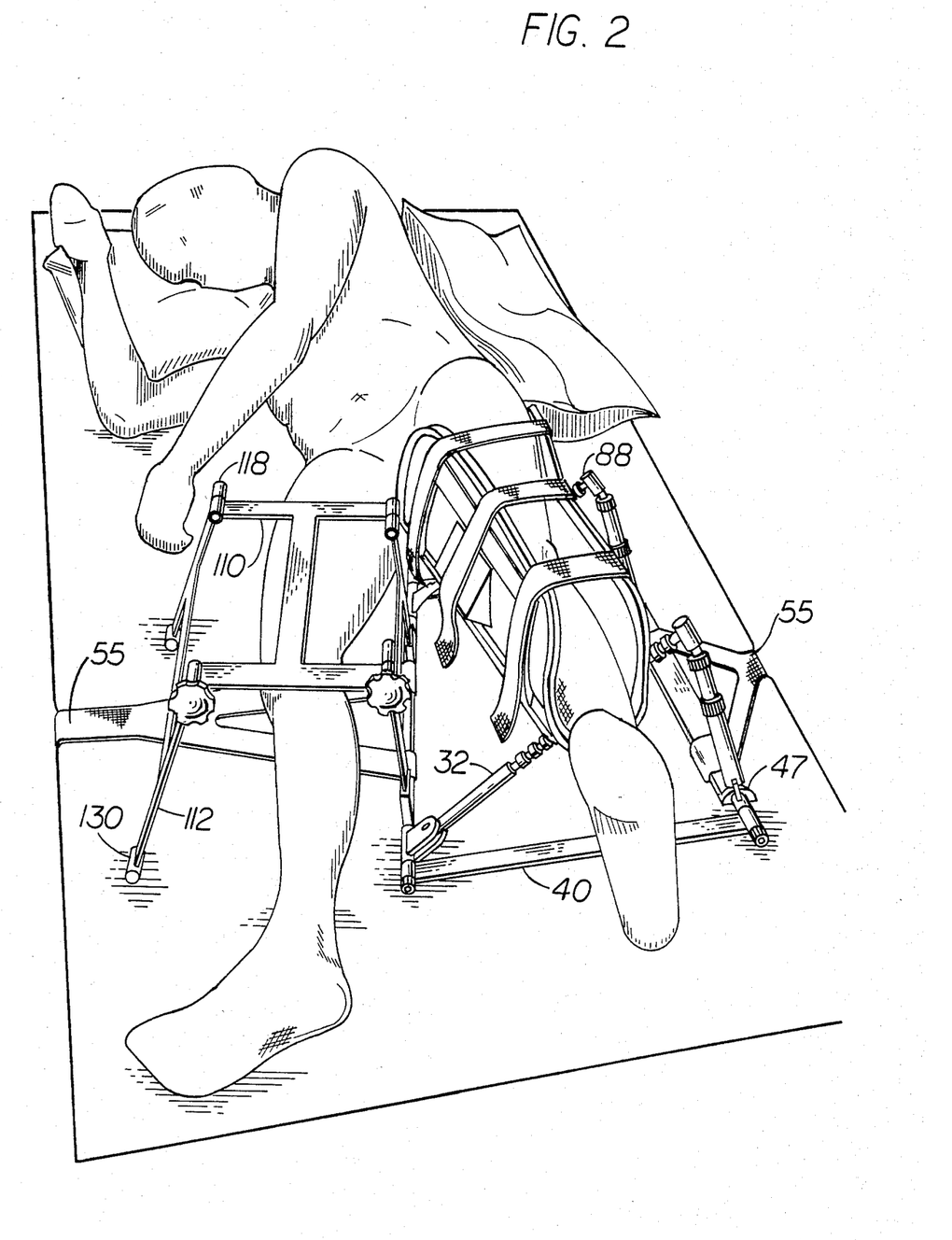
FIG. 2 is a perspective view showing the preferred embodiment of FIG. 1 in use.
Figure 3:
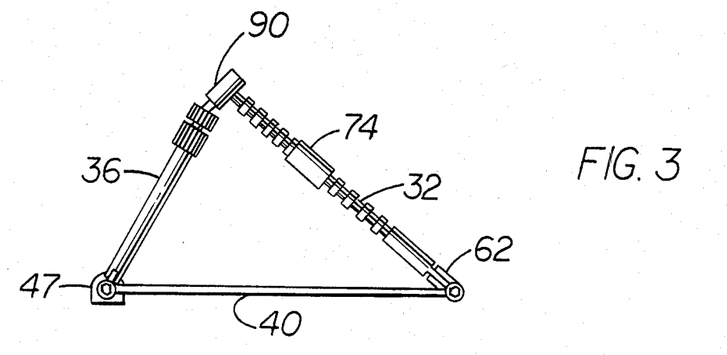
FIG. 3 is a front elevation view of the elevating portion of the preferred embodiment of FIG. 1.
Figure 4:
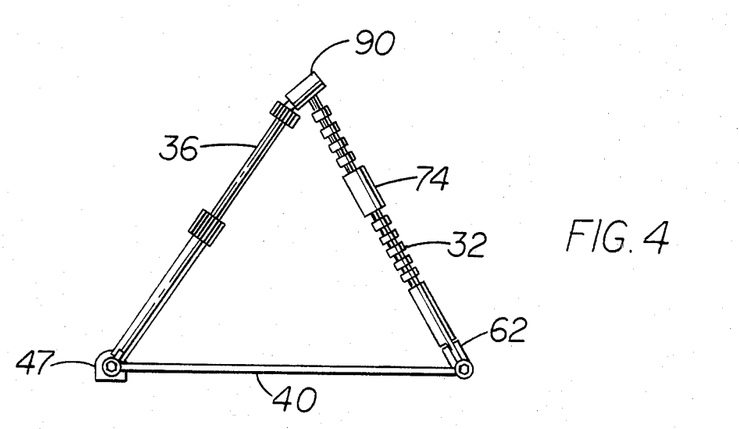
FIG. 4 is a front elevation view similar to FIG. 3 and showing the elevating portion raised to a different height.
Figure 5:
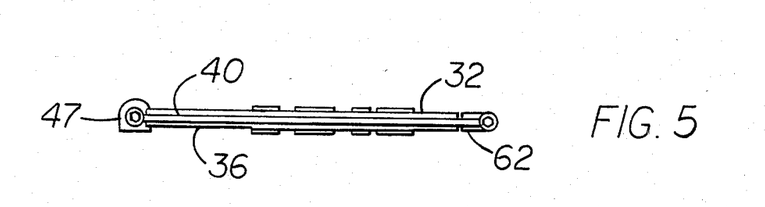
FIG. 5 is a front elevation view of the elevating portion of the preferred embodiment of FIG. 1 showing the elevating portion in an unraised position, i.e., folded flat for storage.

A prefatory overview of the preferred embodiment of the present invention can be gained by reference to FIGS. 1 and 2. FIG. 1 is an exploded perspective view as seen from the foot of the bed. It should be noted that in FIG. 1 the apparatus has been adjusted for use on the right leg of the patient, while FIG. 2 shows the apparatus adjusted to the configuration used on the patient's left leg. The purpose of showing these two configurations is to illustrate that the apparatus is useable on both right legs and left legs. A careful comparison of FIG. 1 with FIG. 2 will reveal that this right-left adaptability is accomplished not by rotating the apparatus 180 degrees in the plane of a flat surface, but instead by rotating various elements about a medial axis 16.

Figure 6:
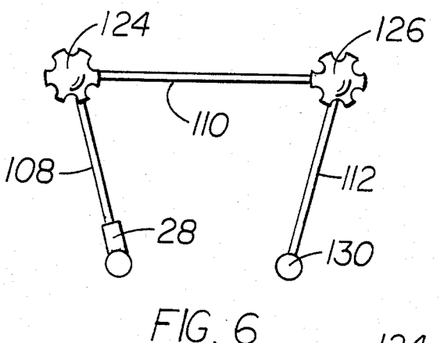
FIG. 6 is a front elevation view of the cage portion of the preferred embodiment of FIG. 1.
Figure 7:
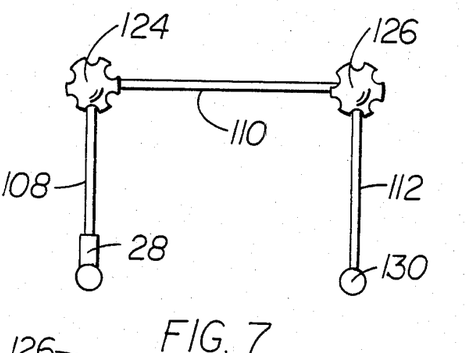
FIGS. 7 and 8 are front elevation views similar to FIG. 6 and showing the cage portion adjusted to other shapes.
Figure 8:
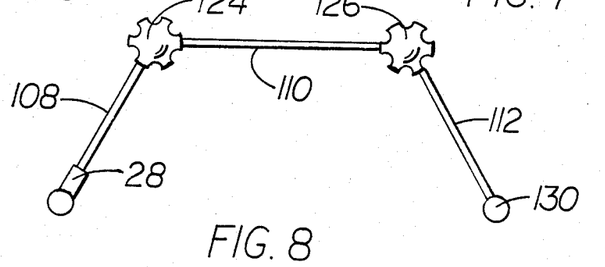
Figure 9:
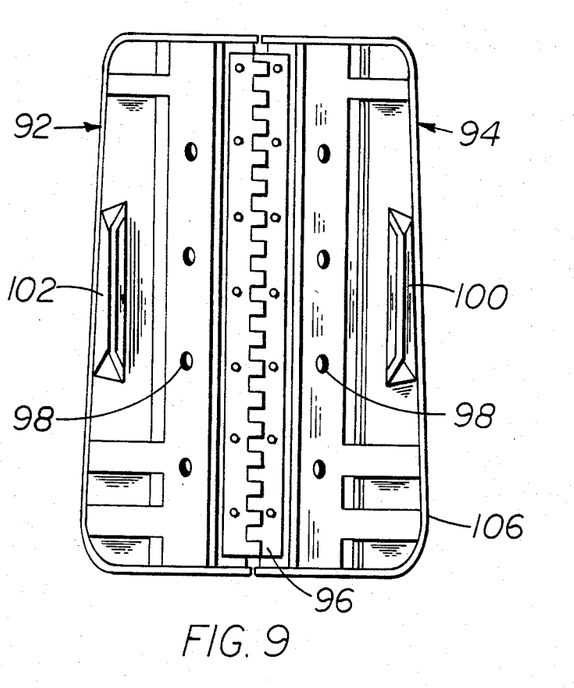
FIG. 9 is a bottom view of the splint portion of the preferred embodiment of FIG. 1.
Figure 10:
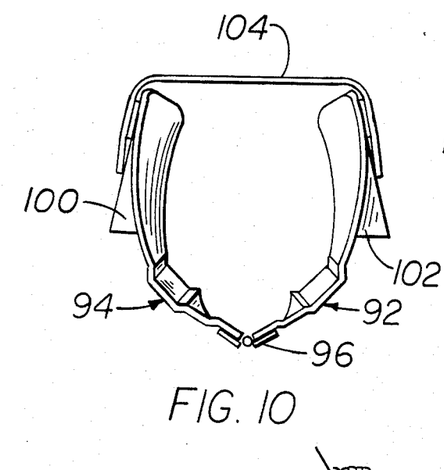
FIGS. 10 and 11 are rear end views of the splint portion of FIG. 9 showing the splint portion adjusted to accommodate legs of different sizes.
Figure 11:
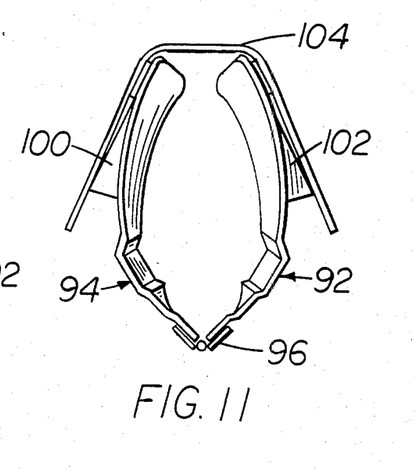

Referring to FIG. 1, it is seen that the apparatus includes three separable portions: the elevating portion 10, the splint portion 12 and the optional cage portion 14. Various aspects of the elevating portion 10 are shown in FIGS. 1-5. The splint portion 12 is shown in FIGS. 9-11, and certain aspects of the cage portion 14 are illustrated in FIGS. 6-8.

Still referring to FIG. 1, the splint portion 12 is affixable to the elevating portion 10 at a selected position along the slot 18 in the splint mounting bar 20 by means of the bolts 22 and the nuts 24. The cage portion 14 may be attached to the elevating portion 10, when the use of the cage portion is indicated, by inserting the tongues 26 into the sockets 28.

Briefly, by way of overview, the apparatus is used as follows. Initially the patient is lying on his back on a flat surface. The elevating portion 10 is then placed under the leg to be rotated. Then the splint portion 12 is aligned beside that leg to determine the selected location on the splint mounting bar 20 at which the splint portion will be placed. At this point a technician raises and holds the leg to be elevated, while the physician attaches the splint portion 12 to the elevating portion.

Thereafter, the technician lowers the leg and the physician secure the leg in the splint portion. Next the physician pulls the knobs 76, 78 to adjust the splint mounting bar 20 to the selected degree of abduction, then releases the knobs to lock the mounting bar in position. Next, the telescoping support arms 34, 36 are pulled out from inside the base where they rest, and they are adjusted to provide the desired degree of elevation.

In the following paragraphs the elevating portion 10, the splint portion 12 and the cage portion 14 will be described in greater detail.

The elevating portion includes a proximal member 38 and a distal member 40. The proximal member 38 has an end portion 42 at its lateral end, and the distal member 40 has an end portion 44 at its lateral end. The end portions 42, 44 are bored to hold internally-threaded tubes that extend from the ends of the strap mount 47. The bolts 45, 46 screw into the tubes to hold the proximal member 38 and the distal member 40 to the strap mount 47. The strap mount 47 includes notches, of which the notch 53 is typical, to permit the elevating portion to be secured to the bed by means of a strap 55, as shown in FIG. 2.

A collar 57 surrounds the tube that extends from the end of the strap mount 47, and the telescoping support arm 36 is attached to this collar 57 by a clevis 50. A similar mounting is used for the telescoping support arm 34.

This mounting arrangement for the telescoping support arms 34, 36 permits those arms to be moved to any angular position with respect to the proximal member 38 and the distal member 40.

Similarly, the medial end of the proximal member 38 includes an end portion 54, and the medial end of the distal member 40 includes an end portion 56. The end portion 54 and the end portion 56 are bored to hold a tube 58 which connects the medial end of the proximal member 38 with the medial end of the distal member 40. The sleeve 62 is mounted for rotation on the tube 58, and the sleeve 62 includes the clevis 66 by which the grooved elevator arm 32 is hinged to the sleeve 62. The sleeve 60 is also mounted for rotation on the tube 58, and the grooved elevator arm 30 is rigidly attached to the sleeve 60. A third sleeve 64 is mounted on the tube 58 for rotation independent of the sleeves 60, 62.

The arrangement described in the preceeding paragraph permits the grooved elevator arm 32 to be rotated to any angular position with respect to the distal member 40, but permits the grooved elevator arm 30 to be rotated about the medial axis 16 only.

The telescoping support arms 34, 36 are similar to those used on camera tripods; they can be unlocked to permit lengthwise adjustment and can be locked to maintain a selected length.

A slidable lock 72 is slidably mounted on the grooved elevator arm 30. The slidable lock 72 includes the spring-loaded plunger 76 that is urged perpendicularly to the grooved elevator arm 30 so as to engage a selected one of the the notches in the elevator arm 30.

Likewise, the slidable lock 74 is slidably mounted on the grooved elevator arm 32 and includes the spring-loaded plunger 78 for locking the slidable lock 74 at a chosen position along the grooved elevator arm 32.

The splint mounting bar 20 is pinned at its ends to the slidable lock 72 and the slidable lock 74 by means of the pins 80, 82 respectively.

The grooved elevator arm 30 includes a ball 84 at its free end, and the telescoping supporting arm 34 includes a spring-loaded cage 88 at its free end for capturing and holding the ball 84. The ball 84 and the spring-loaded cage 88 together constitute a quick-disconnect ball joint. Likewise, the grooved elevator arm 32 includes the ball 86 at its free end and the telescoping support arm 36 includes the spring-loaded cage 90 at its free end, for capturing and retaining the ball 86.

The splint portion 12, shown in greater detail in FIGS. 9-11 includes a right side 92 and a left side 94 which are mirror images of each other. The two sides 92, 94 are joined together by the piano hinge 96. Each side includes mounting holes of which the holes 98 are typical. The mounting holes 98 are used for attaching the splint portion 12 to the elevating portion 10 in either of two positions to hold the leg in either internal or external rotation.

The sides 92, 94 also include the handles 102, 100, respectively.

FIGS. 10 and 11 show the wide range of adaptability that can be achieved with the splint of the preferred embodiment. In FIG. 10, the splint is opened relatively wide to receive a large leg, while in FIG. 11 the splint is less widely opened to receive a thinner leg. In all cases, the splint portion is positioned along the leg in such a manner that the splint portion extends both above and below the knee, so as to assist in keeping a leg nearly fully extended. Normally, a layer of flexible foamed plastic is inserted between the leg and the splint portion 12. After the leg has been placed in the splint portion, and the sides 92, 94 have been brought together, the sides are held in that position by the use of straps, of which the strap 104 is typical and that include VELCRO ® fastening material. The handles 100, 102 are then used for lifting the leg.

In the preferred embodiment, the body of the splint portion is molded of ABS plastic, and is provided with a trim strip 106.

As shown in FIG. 1, the cage portion 14 includes, in the preferred embodiment, a medial part 108, a superior part 110 and a lateral part 112. Each of these parts is formed of flat stock and has generally the shape of the letter I. As noted above, the medial part 108 of the cage includes the tongues 26 which slip into the sockets 28 of the elevating portion 10.

The medial part 108 of the cage is hinged to the superior part 110 of the cage by the hinges 114, 116. The hinge pin of the hinge 116 is a bolt whose threaded portion 122 can be screwed into a threaded hole in the medial part 108 of the hinge 116 so that when the adjusting knob 124 is turned in one direction, the halves of the hinge will be tightly drawn together so as to lock the medial part 108 and the superior part 110 together.

The superior part 110 of the cage is hinged to the lateral part 112 of the cage by the hinges 118, 120. After adjustment to a desired angle, the superior part 110 and the lateral part 112 can be locked together by tightening the adjusting knob 126, which functions in a manner similar to the adjusting knob 124.

Because each of the I-shaped parts 108, 110, 112 is longer than the preceding one (in the proximal-distal dimension) the cage portion 14 can be folded flat for convenient storage. It should be noted that regardless of which leg the cage portion is placed over, the medial part 108 will be on the inside of the leg and the lateral part 112 will be on the outside of the leg.

FIGS. 6-8 illustrate various configurations to which the cage portion 14 can be adjusted to render it suitable for use with legs of different circumferences. The cylindrical feet 128, 130 prevent damage to the bed sheets.

Use of the cage portion 14 is optional at the discretion of the physician, but it should prove to be beneficial in some cases, where excessive movement by a patient is undesirable.

A prime advantage of the apparatus of the present invention is that it continues to maintain the affected leg in the desired position as the patient is rotated to lie on his side. As the patient is rotated, the nurse or technician gently raises the affected leg by lifting the splint by means of the handles 100, 102. When the desired degree of rotation of the patient has been reached, the spring loaded cages 88, 90 are secured to the balls 84, 86 by the nurse. At this point, the patient can be left unattended in the rotated position and with the splint portion 12 fully supported by the elevating portion 10.

Thus, there has been described an apparatus for maintaining the affected leg of a patient in a desired degree of abduction, a fixed degree of external rotation, and a minimum of flexion even when the patient is rotated to his side. By permitting the patient to be rotated in this manner, the apparatus of the present invention greatly increases the patient's comfort and greatly reduces the possibility of accidental dislocations of the hip.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. Apparatus to facilitate turning a patient lying on his back in a bed onto one side while maintaining the opposite leg in a desired orientation with respect to the patient's body, the desired orientation including a chosen degree of abduction, a chosen degree of rotation, and a minimal degree of flexion, said apparatus comprising in combination:

a splint for supporting the opposite leg of the patient in the desired orientation with respect to the patient's body; and, elevating means attached to said splint for elevating the opposite leg of the patient by constraining said splint to move along an arcuate path from an initial position on the bed to an elevated position as the patient is being turned onto his side.

2. The apparatus of claim 1 furthe comprising splint adjustment means for attaching said splint to said elevating means at an orientation chosen to maintain the opposite leg of the patient at a chosen degree of rotation as the patient is being turned onto his side.

3. The apparatus of claim 1 wherein said elevating means further includes abduction adjustment means for adjusting the orientation of said splint means to an orientation chosen to maintain the opposite leg of the patient at a chosen degree of abduction as the patient is being turned onto his side.

4. The apparatus of claim 1 wherein said elevating means further include support means for adjustably supporting said elevating means at any of a plurality of elevated positions.

5. The apparatus of claim 1 further comprising cage means connected to said elevating means for restraining the other leg of the patient to lie in a particular position.

6. The apparatus of claim 1 wherein said splint further comprises two elongated arched shells connected by a hinge whose axis extends generally in the direction of elongation.

7. The splint of claim 6 wherein each of said two elongated arched shells includes a handle for use in lifting a body member to which the splint has been applied.

8. Apparatus to facilitate turning a patient lying on his back in a bed onto one side while maintaining the opposite leg in a chosen degree of abduction, a chosen degree of rotation, and a minimal degree of flexion, said apparatus comprising in combination:
a splint for supporting the opposite leg of the patient, said splint including two elongated arched shells connected by a hinge, the axis of the hinge extending generally in the direction of elongation;
elevating means attached to said splint for elevating the opposite leg of the patient by constraining said splint to move along an arcuate path from an initial position on the bed to an elevated position as the patient is being turned onto his side, said elevating means including abduction adjustment means for adjusting the orientation of said splint to an orientation chosen to maintain the opposite leg of the patient at a chosen degree of abduction as the patient is being turned onto his side, said elevating means further including support means for adjustably supporting said elevating means at any of a plurality of elevated positions; and,
splint adjustment means for adjustably affixing said splint to said elevating means at an orientation chosen to maintain the opposite leg of the patient at a chosen degree of rotation as the patient is being turned onto his side.

* * * * *